United States Patent [19]
Stanley et al.

[11] Patent Number: 5,783,207
[45] Date of Patent: Jul. 21, 1998

[54] SELECTIVELY REMOVABLE NICOTINE-CONTAINING DOSAGE FORM FOR USE IN THE TRANSMUCOSAL DELIVERY OF NICOTINE

[75] Inventors: Theodore H. Stanley, Salt Lake City; Brian Hague, West Valley City, both of Utah

[73] Assignee: University of Utah Research Foundation, Salt Lake City, Utah

[21] Appl. No.: 795,359

[22] Filed: Feb. 4, 1997

Related U.S. Application Data

[63] Continuation of Ser. No. 439,127, May 11, 1995, abandoned, which is a continuation-in-part of Ser. No. 333,233, Nov. 2, 1994, abandoned, which is a continuation of Ser. No. 152,396, Nov. 12, 1993, abandoned, which is a division of Ser. No. 403,751, Sep. 5, 1989, Pat. No. 5,288,497, which is a continuation-in-part of Ser. No. 60,045, Jun. 8, 1987, Pat. No. 4,863,737, which is a continuation-in-part of Ser. No. 729,301, May 1, 1985, Pat. No. 4,671,953.

[51] Int. Cl.$^6$ .......................... A61K 9/68; A61K 31/465
[52] U.S. Cl. .......................... 424/440; 424/439; 424/441; 514/343; 514/356; 514/813; 514/948
[58] Field of Search .......................... 424/439, 440, 424/441; 514/343, 356, 813, 948

[56] References Cited

U.S. PATENT DOCUMENTS

| | | | |
|---|---|---|---|
| 122,507 | 1/1872 | Wills | 424/441 |
| 4,311,722 | 1/1982 | Vink et al. | 426/660 |
| 4,389,393 | 6/1983 | Schor et al. | 424/19 |
| 4,452,825 | 6/1984 | Klacik et al. | 426/658 |
| 4,515,769 | 5/1985 | Merritt et al. | 424/49 |
| 4,671,953 | 6/1987 | Stanley et al. | 424/440 |
| 4,749,575 | 6/1988 | Rotman | 424/441 |
| 4,806,356 | 2/1989 | Shaw | 424/440 |
| 4,885,173 | 12/1989 | Stanley et al. | 424/440 |
| 5,004,601 | 4/1991 | Snipes | 424/78 |
| 5,035,252 | 7/1991 | Mondre | 132/321 |
| 5,048,544 | 9/1991 | Mascarelli et al. | 131/270 |
| 5,135,752 | 8/1992 | Snipes | 424/435 |
| 5,135,753 | 8/1992 | Baker et al. | 424/435 |
| 5,139,790 | 8/1992 | Snipes | 424/435 |
| 5,176,151 | 1/1993 | Harding | 128/842 |
| 5,244,668 | 9/1993 | Snipes | 424/435 |

FOREIGN PATENT DOCUMENTS

| | | |
|---|---|---|
| 644574 | 9/1993 | Australia. |
| 2230439 | 10/1990 | United Kingdom. |
| 2255892 | 11/1992 | United Kingdom. |
| 91/06288 | 5/1991 | WIPO. |
| 91/09599 | 7/1991 | WIPO. |
| 92/10147 | 6/1992 | WIPO. |

*Primary Examiner*—Raj Bawa
*Attorney, Agent, or Firm*—Workman, Nydegger & Seeley

[57] ABSTRACT

The present invention relates to a selectively removable nicotine-containing dosage form for use in the transmucosal delivery of nicotine to a patient. More specifically, the present invention is directed to a nicotine-containing dosage-form comprising an attached holder member which may be used to manipulate the dosage form within the mouth of the patient as part of an effective smoking cessation program or in situations where smoking is undesirable or not permitted. Nicotine is released from a dosage form and absorbed through the intra-oral mucosal surfaces as the nicotine-containing matrix releases nicotine within the user's mouth. The user may selectively insert and remove the dosage form as desired to control the release of nicotine. In addition, the user may manipulate the dosage form by use of the holder means in such a manner to meet the user's psychological need or desire for ritualistic oral stimulation similar to cigarette smoking.

19 Claims, 2 Drawing Sheets

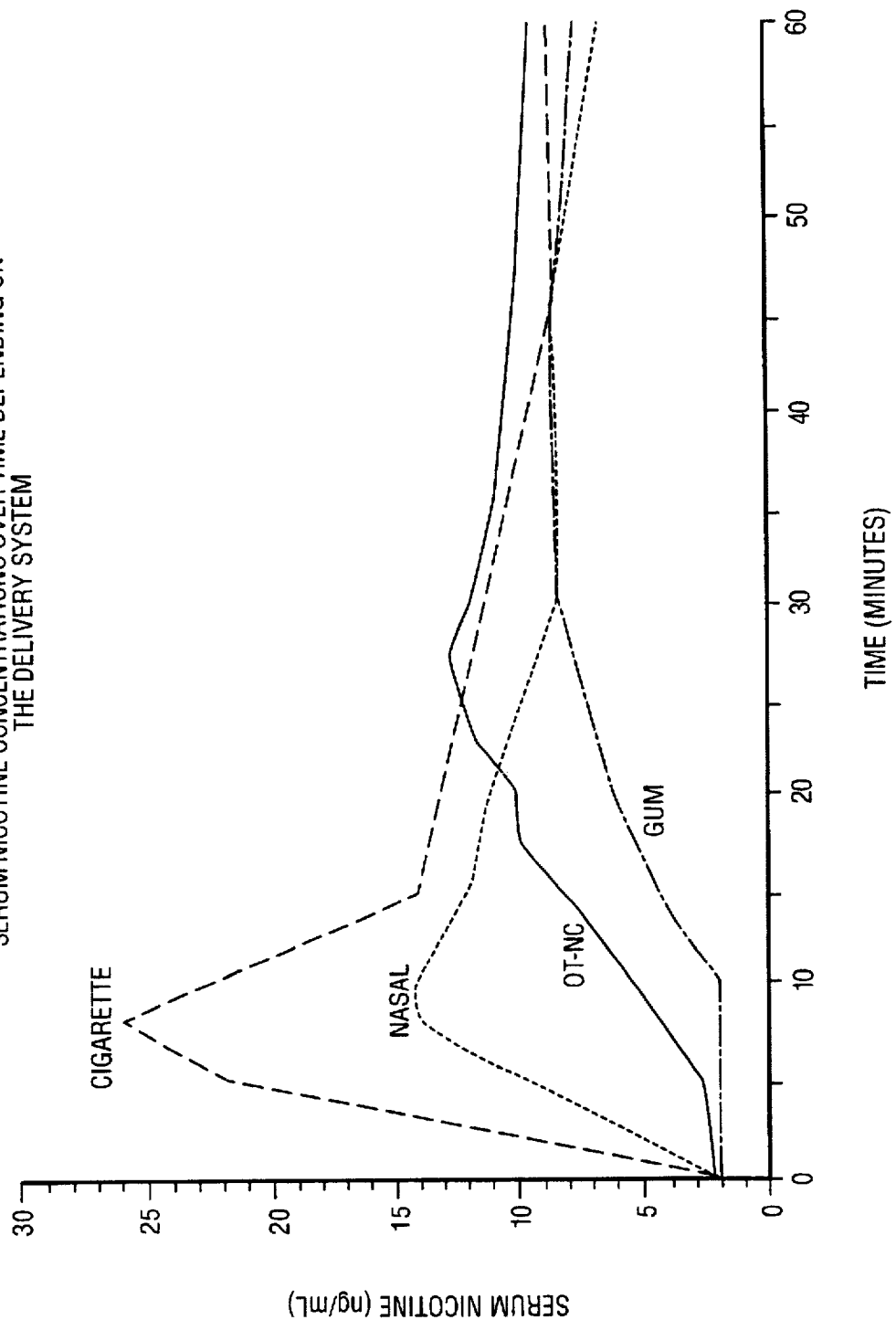

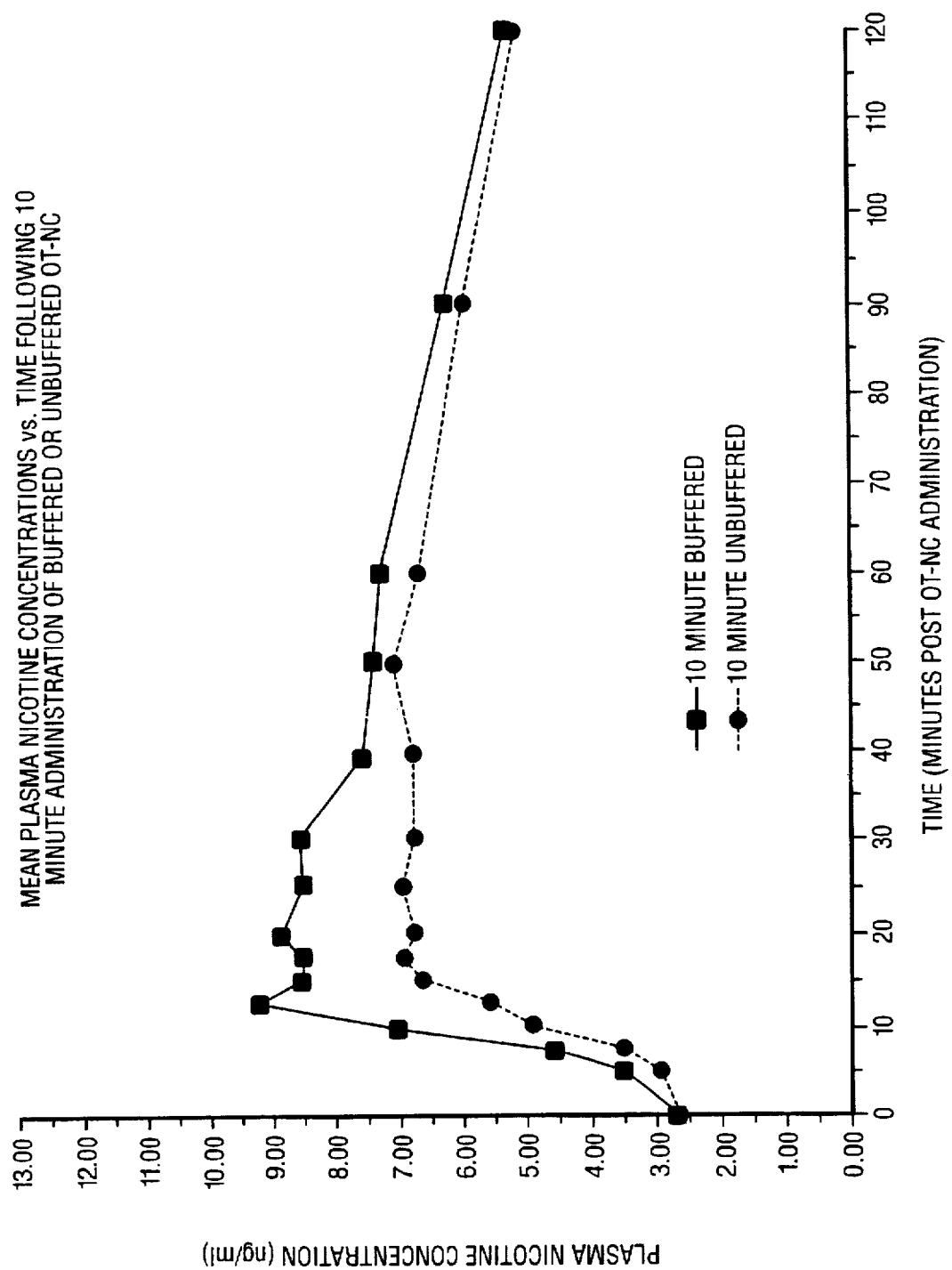

SELECTIVELY REMOVABLE NICOTINE-CONTAINING DOSAGE FORM FOR USE IN THE TRANSMUCOSAL DELIVERY OF NICOTINE

RELATED APPLICATIONS

This application is a continuation of U.S. application Ser. No. 08/439,127, filed May 11, 1995, now abandoned, which is a continuation-in-part application of application Ser. No. 08/333,233, filed Nov. 2, 1994, now abandoned, which is a continuation of application Ser. No. 08/152,396, filed Nov. 12, 1993, now abandoned, which is a divisional of application Ser. No. 07/403,751, filed Sep. 5, 1989, now issued as U.S. Pat. No. 5,288,497, incorporated herein by reference, which is a continuation-in-part of application Ser. No. 07/060,045, filed Jun. 8, 1987, now issued as U.S. Pat. No. 4,863,737, incorporated herein by reference, which is a continuation-in-part of application Ser. No. 06/729,301, filed May 1, 1985, which issued as U.S. Pat. No. 4,671,953, incorporated herein by reference.

BACKGROUND OF THE INVENTION

1. The Field of the Invention

The present invention relates generally to a cigarette substitute for administering a dose of nicotine. More specifically, the present invention is directed to a nicotine-containing dosage-form having a holder which may be used as part of an effective smoking cessation program or in situations where smoking is undesirable or not permitted.

2. Background of the Invention

Nicotine is a naturally occurring drug found in tobacco which has both stimulant and depressant effects in the peripheral and central nervous systems. Nicotine can thus be included in a broad category of CNS-acting drugs. Nicotine occurs as a basic, colorless to pale yellow, very hygroscopic, oily, volatile liquid that has an unpleasant pungent order and a sharp, burning, persistent taste. Nicotine forms salts with almost any acid and therefore exists in a variety of salt forms. Nicotine is considered to be very toxic and toxic effects develop rapidly following an acute overdose. When nicotine is obtained from tobacco, as by chewing, snuffing or smoking, the amount of nicotine absorbed into the body generally does not build up to a toxic level.

Nicotine can be introduced into the body through many different routes. One of the most popular versions of nicotine use involves the smoking of cigarettes. When the tobacco in a cigarette is ignited, the combustion process causes the release of nicotine vapors. The nicotine in cigarette smoke, suspended on minute particles of "tar" is quickly absorbed through the lung. The absorption of nicotine into the body through cigarette smoke is almost as quick as intravenous administration, with the nicotine reaching the brain within eight seconds after inhalation of the tobacco smoke.

Unfortunately, introducing nicotine into the body in this manner also introduces many other compounds into the body as well. The combustion process of tobacco is complex with about 4,000 compounds being generated during combustion. Among the compounds being generated are those which produce highly undesirable effects such as carbon monoxide, carbon dioxide, nitrogen oxides, ammonia, and many other substances. In addition, many substances are left in the lungs as "tar." The variety of substances generated by burning tobacco include many which are believed to have serious long term health effects. Because of this, in recent years smoking has been increasingly disfavored, and because of second hand inhalation, restrictions have been placed on where an individual may smoke.

Because of these and other undesirable side effects, many attempts have been made to provide acceptable substitutes to cigarettes. Most of these substitutes contain nicotine which is generally considered to be the dependence-producing component in tobacco. Other factors such as social reinforcement, environmental factors (e.g. advertising), and learning behavior may also contribute to tobacco dependence.

Most heavy smokers seem to behave as if they are attempting to adjust the concentration of nicotine within relatively narrow limits. For example, when cigarettes with a relatively high content of nicotine are given to heavy smokers, they tend to reduce the number of cigarettes smoked and alter their inhalation patterns thereby achieving concentrations of nicotine in the blood plasma which are only slightly greater than those to which they are accustomed. Similarly, when heavy smokers are given cigarettes with a very low nicotine content, they change their pattern of inhaling or increase the number of cigarettes smoked in order to avoid declines in plasma nicotine concentrations. This suggests, that smokers may be best served by cigarette substitutes which allow for the regulation of plasma nicotine concentrations within specified ranges which mimic cigarettes.

Cessation of the use of tobacco may be followed by a withdrawal syndrome which varies from person to person in intensity and specific signs and symptoms. Although there is wide variability, the most consistent signs and symptoms are a craving for tobacco, irritability, anxiety, restlessness, and difficulty in concentrating. Drowsiness, headaches, increased appetite, insomnia, and gastrointestinal complaints are also common. The use of nicotine supplements during this withdrawal time has been shown, in some cases, to increase the rate of success for those wishing to quit smoking.

Substitutes currently available include nicotine gum, sublingual lozenges, tablets, nasal sprays, vapor inhalers and patches. These substitutes rely on the fact that nicotine is readily absorbed through the mucosa and skin. Because nicotine is a strong base, its absorption in the stomach is limited unless the pH is raised. Intestinal absorption is more efficient than absorption in the stomach, but nicotine is rapidly and extensively metabolized during the first pass through the liver.

The available substitutes, while eliminating the health risks associated with cigarette smoking, do not fully meet the needs of a smoker.

When nicotine gum is used by smokers, they are often encouraged to chew one piece of gum whenever they have the urge to smoke. The instructions generally suggest that the gum should be chewed very slowly until a slight tingling in the mouth is perceived. Once this tingling is felt, it is recommended that the user then stop chewing the gum and wait until this tingling is almost gone (usually within about one minute). This chewing procedure is then repeated periodically for about thirty minutes. This chewing technique is designed to provide constant, slow buccal absorption of nicotine from the gum. By providing slow, constant absorption, nicotine levels in the blood stream can be maintained at a constant level. While there is some evidence indicating that low constant blood levels of nicotine relieves some of the symptoms of nicotine withdrawal, a smoker's craving for tobacco is not mitigated by a relatively low, constant level of nicotine. This is because the nicotine levels derived from smoking are dramatically different in terms of the concentration of nicotine in the blood stream over time from the nicotine levels in the blood stream achieved when nicotine gum is used.

When nicotine is received through smoking, the rapid absorption of the nicotine through the lungs results in an initial peak of nicotine in the blood stream which then subsequently trails off. The blood level peak produced by cigarettes is both higher and sharper than the steadier levels which are obtained from gum or transdermal systems. The initial peak in nicotine concentrations in the blood from smoking is generally between thirty to forty nanograms per milliliter. Furthermore, this peak is attained within about ten minutes. Studies have shown that quick-rise effects are probably necessary for more complete relief from craving in the early stages of cigarette withdrawal. See Russell, M. A. H., In Nicotine Replacement: A Critical Evaluation, Pomerleau, O. F. and Pomerleau, C. S., Eds., Alan R. Liss, Inc., New York, 1988, pp. 63–94. Russell indicates that a rise in the nicotine blood level of at least ten nanograms per milliliter in ten minutes is required to obtain postsynaptic effects at nicotine receptors in the CNS and at autonomic ganglia. These postsynaptic effects may be responsible for the drug-like "high" feelings such as lightheadedness or dizziness experienced by cigarette smokers. Thus, when nicotine can be delivered in a manner which reproduces or mimics the manner in which nicotine is delivered through cigarette smoking, the smoker's craving for cigarettes may be reduced. The slow, constant absorption produced by the intermittent chewing of nicotine gum, fails to achieve this result.

In an effort to mimic the manner in which nicotine is distributed through smoking a cigarette, a user can more aggressively chew the nicotine gum. This, however, is generally not recommended because chewing the gum too rapidly can cause excessive release of nicotine resulting in adverse effects similar to those of excessive smoking such as nausea, hiccups, and irritation of the throat. Chewing nicotine gum aggressively will result in a large amount of nicotine being swallowed because more nicotine is released than can readily be absorbed at the buccal cavity site. If too much nicotine is swallowed, the resultant nausea will most likely cause vomiting. Nicotine gum is thus unable to safely provide a nicotine plasma concentration curve similar to that achieved through smoking cigarettes.

In addition, the use of nicotine gum does not address the psychological needs of the smoker to have something which is placed into the mouth and removed from the mouth in a ritualistic manner. Nicotine gum may also be difficult to tolerate as a long-term treatment. The usefulness of nicotine gum formulations are limited because they taste bad, cannot be used effectively by denture wearers, and may lead to mouth ulcers and heartburn. Furthermore, because of the unique chewing regime which must be imposed to adequately regulate nicotine concentrations in the blood, nicotine gum may be difficult to use in order to regulate nicotine levels within a relatively narrow plasma concentration such as that desired by heavy smokers. Tablet-type smoking substitutes suffer from similar drawbacks.

Transdermal patches which contain nicotine have also been developed. These patches are designed to be placed on one's skin. The nicotine in the patch is then absorbed through the skin. Because of the simplicity of nicotine patches, patient compliance is usually high. Transdermal patches have been developed that can be changed regularly. For instance, patches which are to be changed once a day or, perhaps once a week, are available. Nicotine patches are able to deliver nicotine in such a way that a steady state nicotine concentration can be maintained in the blood plasma. This eliminates the fluctuations that can occur when using gum or tablets which must be taken regularly.

As with the nicotine gum, the delivery of nicotine into the body is at a relatively constant rate. These patches are thus unable to duplicate the plasma nicotine concentration curve obtained through smoking a cigarette. In addition, severe poisoning can result from improper use of these patches. For example, if an individual has a patch applied and then smokes several cigarettes, the plasma nicotine concentration will be much greater than what the individual is used to. This may result in nicotine overdose.

Other considerations must be taken into account when nicotine patches are used. The lethal dose unit for an average adult is about sixty milligrams of nicotine. One cigarette delivers about one milligram of nicotine. Therefore, a patch that is to be effective for twelve or twenty-four hours may contain between thirty and sixty milligrams of nicotine. This presents a safety concern as this represents a potentially lethal dose if nicotine delivery from the patches were significantly increased. This might occur if the patient were to lay on a heating pad or warm water bed. In addition, if the patch is tampered with or ingested by a child, for example, poisoning may occur. Furthermore, nicotine patches do not provide oral stimulation to address the psychological aspects of cigarette craving.

Thus, while current cigarette substitutes are capable of delivering enough nicotine to help alleviate some physical symptoms of nicotine withdrawal, they fail to provide the quick-rise in nicotine blood concentrations which smoking a cigarette provides. They also fail to address the psychological needs of someone who is trying to quit smoking. Many rituals are developed during years of smoking. One such ritual is the periodic placing of something into and out of a person's mouth and the associated oral stimulation of holding a cigarette in one's mouth.

Additionally, patients are usually under-dosed because the physician does not measure baseline nicotine levels and does not instruct the patient in the proper use of the gums, tablets and/or patches. This may explain the somewhat low level of success with patches and gum. Some studies indicate that only about twenty percent of those using nicotine patches under prescription managed to quit smoking. Other studies using nicotine gum showed similar results. Nicotine nasal spray also causes problems such as pain or irritation to the nasal mucosa, and while adequate plasma levels of nicotine may be realized, the oral gratification and sensory ritualistic behaviors are left unsatisfied.

BRIEF SUMMARY AND OBJECTS OF THE INVENTION

It is one object of the present invention to provide a nicotine-containing dosage form which can be utilized as part of a long-term smoking cessation program.

Another object of the present invention is to provide a nicotine-containing dosage form which is suitable for use as a smoking substitute whenever smoking is not allowed or desired.

A further object of the present invention is to provide a nicotine-containing dosage form which can maintain nicotine plasma concentrations within a range which alleviates smoking withdrawal symptoms.

A still further object of the present invention is to provide a nicotine-containing dosage form which can provide nicotine plasma concentrations similar to those achieved by smoking a cigarette.

Yet another object of the present invention is to provide a nicotine-containing dosage form which addresses some of the psychological needs of an individual who desires to quit smoking.

A still further object of the present invention is to provide a nicotine-containing dosage form which is suitable for use by those wearing dentures or other dental appliances.

Another object of the present invention is to provide a nicotine-containing dosage form which is easy to use so as to promote patient compliance.

Yet another object of the present invention is to eliminate the craving for a cigarette by allowing the patient to self-dose the amount of nicotine to overcome the person's individual craving.

It is yet another object of the present invention to provide a nicotine-containing dosage form which can be used in conjunction with a patch so that the individual can control the dosage to treat breakthrough cravings as they occur.

It is a still further object of the present invention to provide a nicotine-containing dosage form which allows patients experiencing a relapse to control occasional urges without raising the baseline nicotine plasma concentration levels.

To achieve the foregoing objects, and in accordance with the invention as embodied and broadly described herein, a nicotine-containing dosage form is provided. The dosage form is configured having a nicotine-containing composition attached to a holder member. Nicotine is released from the dosage form and absorbed through the intra-oral mucosal surfaces as the nicotine-containing composition releases nicotine within a user's mouth. The holder member facilitates insertion and removal of the dosage form into and out of a user's mouth. The user can selectively insert and remove the dosage form as desired to selectively control the release of nicotine to satisfy the user's individual craving. In addition, the user can insert and remove the dosage form in a manner which meets the user's psychological need or desire for ritualistic oral stimulation similar to cigarette smoking.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which:

FIG. 1 is a serum nicotine concentration comparison demonstrating the blood plasma level changes in individuals after administration of cigarettes, nasal sprays, gum and the present invention;

FIG. 2 is a comparison graph demonstrating buffered versus unbuffered absorption rates.

DETAILED DESCRIPTION OF THE PREFERRED EMBODIMENTS

The present invention is related to methods of manufacture and compositions which facilitate the transmucosal delivery of nicotine to a patient for use as either a smoking substitute or an aid to smoking cessation. Simply stated, the present invention relates to a selectively removable nicotine-containing dosage form permitting transmucosal delivery of nicotine through the mucosal tissues of the mouth, pharynx, and esophagus. The nicotine-containing dosage form of the present invention is capable of delivering nicotine into a patient's blood in a manner which results in attainment of blood nicotine concentrations similar to the blood nicotine concentrations attained through smoking cigarettes to thereby address the physical cravings for nicotine which a smoker develops. In addition, the nicotine-containing dosage form of the present invention provides a patient the opportunity, if desired, for physical manipulation and oral stimulation associated with repeated insertion and removal of the dosage form into and out of the patient's mouth to thereby address some of the psychological cravings which a smoker develops.

The present invention overcomes several of the limitations associated with either nicotine-containing transdermal delivery systems or nicotine-containing gum, tablet, nasal spray, or lozenge delivery systems. One of the primary advantages of the present invention is the ability to selectively vary the amount of nicotine released from the dosage form over time through, for example, patient-controlled behavior such as varying the rate of consumption of the dosage form or removing the dosage form from the mouth and reinserting it and/or through design adaptations which affect the concentration of absorbable nicotine released from particular portions of the dosage form.

With the nicotine-containing dosage form of the present invention, it is possible to achieve a relatively rapid initial increase in blood nicotine concentration followed by a period of maintenance of a lower blood nicotine concentration and thereby simulate the pattern attained by smoking a cigarette. Thus, the nicotine-containing dosage form of the present invention may provide a more satisfying alternative to smoking than presently available nicotine delivery systems. This ability is demonstrated in FIG. 1 in which the effect of the administration of several popular dosage forms is demonstrated. The initial peak followed by a gradual diminishment of serum nicotine after smoking a cigarette is shown. Although the nasal spray most closely emulates the cigarette line on the graph, nasal sprays do not provide the psychological benefits of an oral dosage form. Of the oral dosage forms tested, the present invention has the greatest potential for approximating the physiological and psychological effects of cigarettes. By moderating the speed and intensity of sucking on the dosage form, the serum level can be altered to satisfy an individuals unique craving.

One advantage of the present invention is the ability to address the psychological cravings of a cigarette smoker to handle an object which is ritualistically inserted into, held within, and removed from the mouth. The nicotine-containing dosage forms of the present invention comprise a holder member, such as a stick, and a nicotine containing composition attached to the stick. The holder member facilitates selective insertion and removal of the dosage form into and out of a patient's mouth such that a desired physical and psychological effect may be achieved. Unlike nicotine-containing gum, tablets, or lozenges, the dosage form of the present invention can easily be removed to assess the physical effects of the absorbed nicotine, temporarily cease the absorption of nicotine, or to inspect the size and condition of the dosage form at any time. In addition, the holder member prevents inadvertent swallowing of the dosage form and facilitates positioning of the dosage form in a comfortable and adjustable fashion within the oral cavity. Thus, local mucosal irritation from continued contact with nicotine-containing gum, lozenges, or tablets may be avoided by using the holder member to re-position the dosage form within the oral cavity as desired.

The present invention may be used as a smoking substitute by a person in a situation where smoking is either not permitted or not desirable. In this situation, the nicotine-containing dosage form of the present invention provides a satisfying alternative to smoking a cigarette by permitting both physical and psychological simulation of the smoking experience. The present invention may also be used by persons who desire to stop smoking but experience difficulties due to the physical dependence on nicotine and the psychological dependence on the rituals of smoking which have been developed. Such persons must go through a withdrawal period during which the smoking habit is gradually overcome. In this situation, the nicotine-containing dosage form of the present invention provides a means to satisfy both the physical and psychological cravings and, hopefully, permit the person to resist the craving to smoke cigarettes during a withdrawal period sufficient to free the person from the smoking habit.

It may also be desirable to use the nicotine-containing dosage form of the present invention in combination with a transdermal nicotine dosage form as disclosed in U.S. Pat. No. 5,135,753. As taught, the transdermal dosage form provides a consistent release of nicotine to achieve a steady blood concentration level while a second nicotine-containing dosage form intended to be sucked or chewed provides a transient higher concentration of nicotine to thereby more closely simulate the physical effects of smoking a cigarette. It will be appreciated that a combination of a transdermal nicotine dosage form and the nicotine-containing dosage form of the present invention would provide similar physical effects and, at the same time, also address the user's psychological dependence.

Nicotine is available in either the free base or salt form. Nicotine base is readily absorbed through mucosal membranes but is highly volatile. Nicotine salts, on the other hand, are not readily absorbable through mucosal membranes but are much more stable. There is also evidence that ionized species can cross the buccal mucosa via migration between cells. Pharmaceutically acceptable nicotine salts include, but are not limited to nicotine hydrochloride, nicotine dihydrochloride, nicotine sulfate, nicotine monotartrate, nicotine bitartrate, nicotine zinc chloride monohydrate and nicotine salicylate. In an alkaline environment, i.e., pH above about 7, and in the presence of an aqueous medium, such as saliva within the oral cavity, nicotine salts react to form nicotine base. Because saliva normally has a somewhat acidic pH, the incorporation of an alkaline salt into the dosage-form of the present invention will buffer the pH and facilitate the reaction to form readily absorbable nicotine base. Preferred alkaline salts include sodium carbonate, sodium bicarbonate, potassium carbonate, potassium bicarbonate, trisodium phosphate, disodium hydrogen phosphate, sodium oxylate, sodium succinate, sodium citrate, trimethamine and sodium salicylate. The results of buffering are graphically demonstrated in FIG. 2.

In addition to nicotine in a releasable form which is readily absorbed transmucosally, the nicotine-containing compositions in accord with the present invention may contain other ingredients such as flavorings, sweeteners, flavor enhancers, lubricants, binders and fillers. With respect to flavorings, it should be noted that it is desirable to discourage nicotine use by young people. Accordingly, it may be desirable to flavor the nicotine-containing composition in a manner which is unattractive to young people. It may even be desired to provide an unflavored nicotine-containing composition which would be palatable to smokers accustomed to the taste of nicotine yet unattractive to others not so accustomed.

The nicotine-containing dosage form of the present invention consists of any nicotine-containing composition capable of delivering readily absorbable nicotine to the intra-oral mucosal tissues in combination with an attached holder member. The nicotine form that is incorporated into the nicotine-containing composition may be pure nicotine or any compound thereof. The method of manufacture may be any suitable method known in the art including, but not limited to, the addition of a form of nicotine to a dissolvable or non-dissolvable matrix buccal dosage form intended to be sucked or passively dissolved in the mouth. The method of attachment of the holder member similarly may be any suitable method known in the art including, but not limited to, positioning of the holder member within a non-solidified nicotine-containing composition which is subsequently solidified by compression, injection molding or other means, and attachment by gluing, as with confectioner's glue, or bonding by other means, to the pre-manufactured nicotine-containing composition.

One method in accord with the present invention comprises mixing the desired ingredients to form a powdered compressible matrix material which is compressed into an integral solid mass under high pressure. During compression, the mass is attached to a holder member to form a nicotine-containing dosage form. Alternatively, the mass may be attached to a holder member in another manner, such as by gluing with confectioner's glue. A suitable method is taught in U.S. Pat. No. 5,132,114, in the name of the inventors hereof and related to the present application, the disclosure of which has previously been incorporated herein by reference. Nicotine base is a potent, lipophilic, basic, volatile liquid with a low melting point suitable for incorporating into a dosage-form as taught in the above-incorporated U.S. Patent. The method disclosed in U.S. Pat. No. 5,132,114 avoids the use of high temperatures which volatilizes nicotine and also avoids undesired chemical reactions which may occur between the various ingredients in a heated or liquid environment. The method provides for combining dry ingredients, including compressible carbohydrate fillers and binders, by geometric dilution to form a soluble candy-drug mixture which is then compressed to form a solid, dissolvable mass. The compressed mass is held together by physical, rather than chemical, means. The extent of the compressive force can be modified to vary the dissolution rate, i.e., the rate at which the composition dissolves within the oral cavity. In particular, the greater the compressive force used, the slower the dissolution rate will be. The dissolution rate may also be affected chemically with other ingredients. For example, the dissolution rate may be decreased by adding hydrophobic agents such as calcium stearate or the dissolution rate can be increased with the addition of hydrophilic agents or disintegrating agents such as lactose.

In addition, the methods disclosed in U.S. Pat. No. 5,132,114 may include ingredients such as flavorings, sweeteners, flavor enhancers, releasing agents, and buffers. It is preferred that these ingredients be provided in a powder form to facilitate mixing even if the ingredients happen to be insoluble or otherwise chemically incompatible.

One method utilized to produce an embodiment of the present invention involves a nondissolvable matrix into which the nicotine is placed. The nicotine may be in a liquid form or may be held in a liquid carrier for transport through the nondissolving matrix. Examples of appropriate nondissolvable matrices are disclosed in U.S. Pat. No. 5,288,498 by the same inventors which are incorporated by reference herein.

Another method in accord with the present invention comprises mixing the desired ingredients into a dissolvable solid matrix composition containing a permeation enhancer to improve the permeability of the mucosal membranes toward the drug. For example, a suitable method is disclosed in U.S. Pat. No. 5,288,497, in the name of the inventors hereof and related to the present application, the disclosure of which has previously been incorporated herein by reference. As taught in U.S. Pat. No. 5,288,497, a typical "bulk dissolvable matrix" may include hydrogel-, gelatin-, fat-, protein-, wax-based, and/or other dissolvable substances. The desired ingredients may be formed into a solid matrix composition by compression molding, dehydration, freeze drying (lyophilization), pouring into a mold, spraying onto a suitable holder, vapor deposition, or other known techniques.

In addition, U.S. Pat. No. 5,288,497 teaches that either or both the drug and the permeation enhancer may be dispersed uniformly throughout the dissolvable solid matrix composition or may be selectively dispersed, i.e., stratified or coated, to thereby vary the absorption of the drug from selected portions of the dissolvable solid matrix. It will be appreciated that a stratified nicotine-containing composition could be formulated to effect an initial relatively rapid rise in blood nicotine concentration followed by maintenance of a relatively lower blood nicotine concentration. This may be accomplished, for example, by formulating a two-layer composite matrix comprising an inner matrix and an outer matrix. The solubility of the matrices could be different such that the outer matrix is more rapidly dissolved within the oral cavity than the inner matrix.

Alternatively, or in addition, the concentration of nicotine compound within the matrices could be different such that the outer matrix releases a higher quantity of nicotine than the inner matrix. Alternatively, or in addition, the matrices could contain different concentrations of permeation enhancer or different permeation enhancers with different capability to increase the absorption of nicotine through the mucosal surface such that a higher quantity of nicotine is absorbed from the outer matrix than from the inner matrix. In any of these multilayer embodiments, the blood nicotine concentration will rise relatively more rapidly while the patient consumes the outer matrix than while the patient consumes the inner matrix.

Additional selectivity and control of nicotine release and absorption rates could be obtained with more matrix layers and/or combinations of the above-described methods, i.e., varying the matrix dissolvability, varying the permeation enhancement, or varying the drug concentration throughout the matrices. It will be appreciated that more than two layers could also be incorporated into the multilayer nicotine-containing composition to further vary the effect as desired. The presence of additional layers can be indicated by color or flavor changes.

A holder member in accord with the present invention could also be combined with other known dissolvable matrix compositions formulated to release absorbable nicotine at a desired rate when the patient sucks or licks the matrix. For example, compression methods to form nicotine-containing compositions intended to be sucked are taught in U.S. Pat. No. 5,135,753, incorporated herein by reference. The methods taught include direct compression wherein nicotine is adsorbed onto a carrier to facilitate mixing with the other ingredients, which may be in granulated form. Examples 29–36 describe the manufacture of nicotine lozenges using direct compression and granulation methods in which the nicotine is adsorbed onto a carrier resulting in a "dry form" for mixing with other ingredients, all examples include buffering except 29. Example 37 describes a compressed granulated tablet form and example 38 describes a soft, chewable gelatine capsule form. In the formulations disclosed, the amount of nicotine in each dosage form is preferably less than 20 mg., and most preferably between 0.5 to 8.0 mg. to avoid accidental overdosage by swallowing. The presently preferred embodiment utilizes nicotine bitartrate. Although the dosage form of the present invention comprises a holder member which prevents swallowing of the dosage form, it may nevertheless be preferable to keep the nicotine dose in individual dosage forms low to thereby allow a patient to easily selectively control the amount of nicotine ingested by controlling the number of dosage forms used.

As disclosed in the above-referenced patent, the nicotine-containing compositions intended to be sucked are preferably buffered to increase and maintain the percentage of unionized drug to facilitate transport and absorption through the oral mucosa and thereby aid in transmucosal absorption. A preferred formulation is at a pH of 6.8–11. As described above, buffered formulations will include sodium carbonate, sodium phosphate, calcium carbonate, magnesium hydroxide, trimethamine and other substances known in the art.

Buffered nicotine-containing compositions intended to be sucked and formulated by direct compression are also disclosed in published UK patent application GB 2255892A, incorporated herein by reference. The compositions comprise a mixture of directly compressible excipients, a pharmaceutically acceptable salt of nicotine and a base sufficient to maintain the pH level within the patient's mouth at least about 8.5 for at least about 5 minutes. The preparation is mixed with suitable diluents and compressed or compressed with a granulated "core" comprising a portion of the buffering base ingredient.

Another method taught in U.S. Pat. No. 4,806,356, incorporated herein by reference, involves cold compression, extrusion, or drying of a mixture containing an inert filler material, an inert binder material, and a solution of nicotine or nicotine-containing substance dissolved in alcohol to formulate a nicotine-containing lozenge dosage form. Published UK patent application GB 2230439A, incorporated herein by reference, comprises adding a coating to such a nicotine-containing lozenge "core." The coating can, for example, comprise a substance to enhance dissolvability of the composition or a substance to act as local anesthetic and thereby decrease the perceived local irritation from a nicotine absorption site. It will be appreciated that a method similar to the "coating" method could also be used to provide a multi-layer nicotine-containing composition wherein the layers permit nicotine to be released in different amounts or absorbed at different rates similar to the approach discussed above with respect to "stratified" dissolvable solid matrices as taught in U.S. Pat. No. 5,288,497.

In addition, methods for formulating dissolvable nicotine-containing matrices for buccal dosage forms, which melt in the user's oral cavity but are stable in higher shipment and storage temperatures, are taught in a series of related U.S. Pat. No. 5,135,752, No. 5,004,601, No. 5,139,790, and No.

5,244,668, the disclosures of which are herein incorporated by reference. The dissolvable matrices comprise a gel base formed when PEO and colloidal silica are dispersed in molten PEG. Another disclosure of gel-based dissolvable compositions is found in published PCT application DK 90/00280, incorporated herein by reference. The method comprises casting preparations of liquid, homogenous compositions of polysaccharide and/or starches and/or gelatine mixed with solutions of sugar which are allowed to solidify.

Another nicotine-containing formulation which could be attached to a holder member in accord with the present invention is found in published PCT application SE 90/00848, incorporated herein by reference. This disclosure teaches a nicotine-containing composition wherein the nicotine is in the form of an inclusion complex between nicotine and a cyclo compound, preferably a cyclized polysaccharide, and most preferably a β-cyclodextrin. The inclusion complex is stable, has improved taste, less irritant effect, and good bioavailability. No buffering agents are required because the release of nicotine from the inclusion complex is pH-independent.

It will be appreciated that although nicotine is often consumed in cigarette form with the accompanying deleterious effects of tar and smoke, nicotine has been found to have beneficial effects such as treatment of alzheimers disease, colitis, and other gastrointestinal ailments. Although presented as a cigarette substitute, the present invention is also directed to the beneficial administration of nicotine for treatment of these and other ailments.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A selectively removable nicotine-containing dosage form for use in the transmucosal delivery of nicotine to a patient, the dosage form comprising:
   a) a matrix dissolvable in the oral cavity of a patient;
   b) a pharmacologically effective dose of nicotine dispersed in the matrix for absorption through the mucosal tissue of the mouth, pharynx, and esophagus of the patient; and
   c) an attached holder member secured to the matrix, said holder member being so configured as to permit the selective removal and insertion of the dosage form into and out of the patient's mouth without directly handling the matrix, whereby the nicotine-containing dosage form can be manipulated in a manner that mimics manipulation of a cigarette during smoking in order to satisfy a psychological need or desire for ritualistic oral stimulation.

2. A selectively removable nicotine-containing dosage form as recited in claim 1 wherein the dose of nicotine base equivalents is within the range of about 0.1 mg to 20 mg.

3. A selectively removable nicotine-containing dosage form as recited in claim 1 wherein the nicotine is present within the matrix in the form of nicotine base.

4. A selectively removable nicotine-containing dosage form as recited in claim 1 wherein the nicotine is present within the matrix in the form of a nicotine salt compound.

5. A selectively removable nicotine-containing dosage form as recited in claim 1, further comprising a buffering agent dispersed into the matrix, said buffering agent increasing the pH within the oral cavity.

6. A selectively removable nicotine-containing dosage form as recited in claim 1 further comprising a binding agent.

7. A selectively removable nicotine-containing dosage form as recited in claim 1 wherein the matrix further comprises multiple layers of compositions.

8. A selectively removable nicotine-containing dosage form as recited in claim 7 wherein at least two of the multiple layers contain different quantities by weight of dispersed nicotine base.

9. A selectively removable nicotine-containing dosage form as recited in claim 7 wherein at least two of the multiple layers contain different quantities by weight of a dispersed permeation enhancing agent.

10. A selectively removable nicotine-containing dosage form as recited in claim 7 wherein at least two of the multiple layers contain different quantities by weight of a dispersed dissolution enhancing agent.

11. A selectively removable nicotine-containing dosage form as recited in claim 1 further comprising a coating layer containing a dissolution enhancing agent.

12. A selectively removable nicotine-containing dosage form as recited in claim 1 further comprising a coating layer containing nicotine base.

13. A selectively removable nicotine-containing dosage form as recited in claim 1 further comprising a coating layer containing a nicotine salt compound.

14. A selectively removable nicotine-containing dosage form as recited in claim 13 further comprising a buffering agent dispersed within the coating layer.

15. A selectively removable nicotine-containing dosage form as recited in claim 1 wherein the nicotine is dispersed into the matrix such that the concentration of nicotine available for absorption through the mucosal tissue of the mouth, pharynx, and esophagus varies over time as the matrix dissolves in the mouth of the patient.

16. A selectively removable nicotine-containing dosage form as recited in claim 15 wherein the concentration of nicotine within an outer portion of the matrix is greater than the concentration of nicotine within an inner portion of the matrix.

17. A selectively removable nicotine-containing dosage form as recited in claim 1 wherein the rate of dissolution of the matrix varies over time as the matrix is dissolved in the mouth of the patient.

18. A selectively removable nicotine-containing dosage form as recited in claim 17 wherein the rate of dissolution is greater during dissolution of an outer portion of the matrix than during dissolution of an inner portion of the matrix.

19. A selectively removable nicotine-containing dosage form as recited in claim 5 wherein the buffering agent is dispersed into the matrix in varying concentrations by weight.

* * * * *